(12) United States Patent
Gillette

(10) Patent No.: US 8,272,582 B2
(45) Date of Patent: Sep. 25, 2012

(54) SYSTEMS AND METHODS FOR PRODUCING OZONATED WATER ON DEMAND

(76) Inventor: Thomas D. Gillette, Burley, ID (US)

( * ) Notice: Subject to any disclaimer, the term of this patent is extended or adjusted under 35 U.S.C. 154(b) by 907 days.

(21) Appl. No.: 12/210,966

(22) Filed: Sep. 15, 2008

(65) Prior Publication Data

US 2009/0072052 A1 Mar. 19, 2009

Related U.S. Application Data

(63) Continuation-in-part of application No. 10/306,168, filed on Nov. 26, 2002, now Pat. No. 7,425,301.

(60) Provisional application No. 60/333,428, filed on Nov. 26, 2001.

(51) Int. Cl.
*B01B 1/00* (2006.01)

(52) U.S. Cl. ............... 239/398; 422/28; 239/429

(58) Field of Classification Search ............ 422/28; 239/398, 399, 429, 432
See application file for complete search history.

(56) References Cited

U.S. PATENT DOCUMENTS

| | | | | |
|---|---|---|---|---|
| 1,853,045 A | * | 4/1932 | Gnau | ............... 261/76 |
| 3,567,116 A | * | 3/1971 | Lindlof | ............... 239/14.2 |
| 3,774,846 A | * | 11/1973 | Schurig et al. | ............... 239/427.3 |
| 5,054,688 A | * | 10/1991 | Grindley | ............... 239/407 |
| 5,227,184 A | | 7/1993 | Hurst | |
| 5,403,602 A | | 4/1995 | Endico | |
| 5,427,693 A | | 6/1995 | Mausgrover et al. | |
| 5,560,831 A | | 10/1996 | Bladen et al. | |
| 5,683,576 A | | 11/1997 | Olsen | |
| 5,720,905 A | | 2/1998 | Ho | |
| 5,824,274 A | | 10/1998 | Long | |
| 5,843,307 A | | 12/1998 | Faivre et al. | |
| 5,858,430 A | | 1/1999 | Endico | |
| 5,891,499 A | | 4/1999 | Balsano | |
| 5,916,523 A | | 6/1999 | Yan et al. | |
| 5,927,304 A | | 7/1999 | Wen | |
| 5,951,921 A | | 9/1999 | Koganezawa et al. | |
| 6,027,688 A | | 2/2000 | Wainwright | |
| 6,120,822 A | | 9/2000 | Denvir et al. | |
| 6,132,629 A | | 10/2000 | Boley | |
| 6,143,245 A | | 11/2000 | Yan et al. | |
| 6,287,515 B1 | | 9/2001 | Koosman et al. | |
| 6,379,633 B1 | | 4/2002 | Garlick | |

(Continued)

FOREIGN PATENT DOCUMENTS

JP 08103176 4/1996

(Continued)

*Primary Examiner* — Sean E Conley
(74) *Attorney, Agent, or Firm* — David B. Tingey; Kirton | McConkie

(57) ABSTRACT

Systems and methods for producing ozonated water on demand. In particular, these systems comprise a water source, an ozone source, and a nozzle that mixes ozone and water to form a highly concentrated, ozonated water solution. Instead of requiring the ozonated water to be re-circulated to achieve a desired ozone concentration, the nozzle is configured to form the ozonated water solution in a single pass through the nozzle. Additionally, instead of requiring the ozonated water to be discharged into a pressurized tank to increase ozone absorption, the nozzle allows the ozonated water to be openly discharged. In some cases, the nozzle comprises a venturi with multiple ozone inlets to increase mixing. Additionally, in some cases the nozzle comprises a single pass mixing mechanism that mixes the water and ozone to form the high concentrate, ozonated water solution in a single pass through the nozzle.

20 Claims, 11 Drawing Sheets

U.S. PATENT DOCUMENTS

| | | |
|---|---|---|
| 6,506,309 B1 | 1/2003 | Daniels et al. |
| 7,425,301 B2 | 9/2008 | Gillette et al. |
| 2002/0134736 A1 | 9/2002 | Burris et al. |
| 2002/0192110 A1 | 12/2002 | Garlick |
| 2004/0022908 A1 | 2/2004 | Kanaya et al. |
| 2004/0109797 A1 | 6/2004 | Grove |
| 2004/0245281 A1 | 12/2004 | Oke |
| 2007/0163935 A1 | 7/2007 | Chewins |
| 2008/0190825 A1 | 8/2008 | Hengsperger et al. |

FOREIGN PATENT DOCUMENTS

| | | |
|---|---|---|
| KR | 10-2006-0025151 | 3/2006 |

* cited by examiner

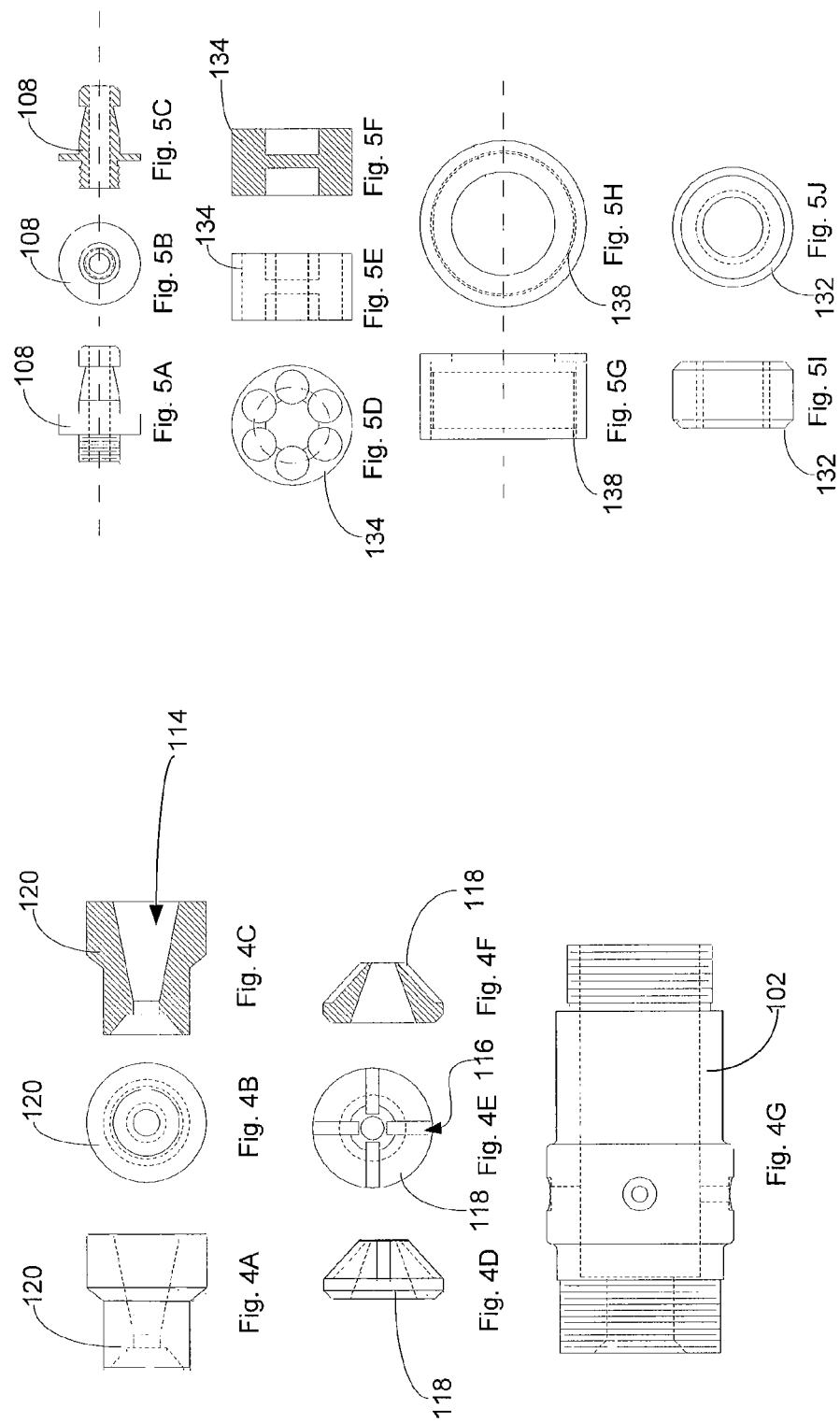

SYSTEMS AND METHODS FOR PRODUCING OZONATED WATER ON DEMAND

RELATED APPLICATIONS

This is a continuation-in-part application of U.S. patent application Ser. No. 10/306,168, filed Nov. 26, 2002, entitled "METHOD AND DEVICE FOR PRODUCING OZONE SANITATION OF VARIOUS OBJECTS," which claims priority to U.S. Provisional Application Ser. No. 60/333,428, filed Nov. 26, 2001, entitled "OZONE SANITATION UNIT;" the entire disclosures of both the Ser. No. 10/306,168 and the 60/333,428 applications are hereby incorporated by reference.

BACKGROUND OF THE INVENTION

1. Field of the Invention

This application relates to systems and methods associated with ozonated water. In particular, this application discusses systems and methods for producing an ozonated water solution (or ozonated water) on demand.

2. Background of the Invention and Related Art

Currently, techniques exist for the production of ozonated water. For instance, some conventional techniques for producing ozonated water involve circulating water through a circulation loop that includes a venturi, which is connected to a supply of ozone. As the water passes through the venturi, ozone gas is sucked, according to Bernoulli's principle, into the water flow. In this manner, the ozone is bubbled through and partially absorbed by the water. After the water has passed through the loop, the ozonated water can then be collected in a pressurized tank and then be re-circulated through the circulation loop several more times to increase the concentration of ozone in the water.

Conventional techniques for producing ozonated water have shortcomings. For instance, because the venturi in many systems simply has a single ozone inlet, ozone tends to be drawn into the water in relatively large bubbles, which prevent the ozone from being efficiently absorbed. For this reason, such systems often require the water to be re-circulated through the circulation line several times before the ozone concentration of the water is high enough for a desired use. Accordingly, such systems can be time consuming to use. Additionally, such systems often produce ozonated water that has a low or unknown ozone concentration. Moreover, because only a relatively small amount of the ozone in the bubbles actually diffuses into the water and because ozone tends to be released from ozonated water stored in a tank, such systems often off gas excessive amounts of ozone.

Because ozone gas, even in small concentrations, can be dangerous to health and be highly corrosive to metals and other materials, off-gassed ozone from an ozonated water system is generally reduced to oxygen through the use of an ozone destructor. Conventional ozone destructors comprise a small, strait, tube that contains a heat source or an ozone catalyst that reduces ozone ($2O_3$) to oxygen ($3O_2$). Also, these conventional destructors are often configured to be disposed on a tank of ozonated water so as to passively receive the off-gassed ozone.

Conventional ozone destructors also have their shortcomings. In one example, conventional ozone destructors do not thoroughly desiccate the air that passes through them. Because many ozone generators function more efficiently when using dry air, destructors that allow air to pass through them and retain a relatively high amount of moisture can reduce the overall efficiency of systems that employ them. In another example, some conventional ozone destructors can be constricted in size and/or be designed to only passively receive air. Accordingly, such conventional destructors can greatly restrict the rate at which air can flow through them. As a result, such destructors can be practical for use only in small areas, such as on top of a tank containing ozonated water. In still another example, some ozone destructors that are configured for larger amounts of air can be large and bulky.

Thus, while techniques currently exist that are used to produce ozonated water and to reduce off-gassed ozone, challenges still exist, including those mentioned above. Accordingly, it would be an improvement in the art to augment or even replace current techniques with other techniques.

SUMMARY OF THE INVENTION

This application relates to systems and methods associated with ozonated water. In particular, this application discusses systems and methods for producing ozonated water on demand as well as for reducing off-gassed ozone. In some implementations, these systems comprise a water source, an ozone source, an ozone destructor, and a nozzle that mixes ozone and water to form a highly concentrated, ozonated water solution. Instead of requiring the ozonated water to be re-circulated through a recirculation loop to achieve a desired ozone concentration, the nozzle is configured to form the ozonated water solution in a single pass through the nozzle. Additionally, instead of requiring the ozonated water solution to be discharged into a pressurized tank to increase ozone absorption, the nozzle allows the ozonated water to be openly discharge. In some cases, the nozzle comprises a venturi with multiple ozone inlets to increase mixing. Additionally, in some cases the nozzle comprises a single pass mixing mechanism that mixes the water and ozone to form the high concentrate, ozonated water solution in a single pass through the nozzle.

As mentioned, the systems can also comprise an ozone destructor. Generally, the ozone destructor comprises a housing that defines a plurality of chambers. In some cases, the destructor comprises a first chamber and a second chamber, where the second chamber is offset to one side of the first chamber. Additionally, the destructor comprises a ventilation mechanism to pull or draw a large amount of air through the destructor. The destructor can also comprise one or more reducing mechanisms (e.g., a heating mechanism or a catalyst) that reduce ozone to oxygen. Among other things, the destructor can also comprise a variety of drying mechanisms, such as a desiccant, a chiller, demisting veins, etc. In this manner, the destructor can render ozone harmless and dry air for use in an ozone generator.

While the described systems, devices, methods, and processes have proven to be particularly useful in the area of sanitizing food products, those skilled in the art can appreciate that the systems, methods, devices, and processes can be used in a variety of different applications and in a variety of different areas, including, but not limited to public water treatment, sanitation of objects, household water treatment, swimming pool and spa treatment, fish farming, ice manufacturing, municipalities, sewage treatment, lake/river treatment, and so forth.

These and other features and advantages will be set forth or will become more fully apparent in the description that follows and in the appended claims. The features and advantages may be realized and obtained by means of the instruments and combinations particularly pointed out in the appended claims. Furthermore, the features and advantages of the described systems, methods, and devices may be learned by the practice of the invention or will be obvious from the description, as set forth hereinafter.

BRIEF DESCRIPTION OF THE DRAWINGS

In order that the manner in which the above-recited and other advantages and features of the systems and methods are obtained, a more particular description of the described systems and methods will be rendered by reference to specific embodiments of the systems and methods, which are illustrated in the appended drawings. Understanding that these drawings depict only typical embodiments and are not therefore to be considered limiting in scope, the systems and methods will be described and explained with additional specificity and detail through the use of the accompanying drawings in which:

FIGS. 4A-4G illustrate some views of components used in some embodiments of the described nozzle;

FIGS. 5A-5J illustrate some views of components used in some embodiments of the described nozzle;

In the Figures, the thickness and configuration of components can be exaggerated for clarity. The same reference numerals in different Figures represent the same component.

DETAILED DESCRIPTION OF THE PREFERRED EMBODIMENTS

It will be readily understood that the components of the systems and methods for producing ozonated water on demand and for reducing off-gassed ozone, as generally described and illustrated in the Figures herein, could be arranged and designed in a wide variety of different configurations. Thus, the following more detailed description of the embodiments of the described systems and methods, as represented in FIGS. 1 through 12, is not intended to limit the scope of the systems and methods, as claimed, but is merely representative of presently preferred embodiments.

To better set forth the concepts and scope of the described systems and methods, the following more detailed description is separated into two sections. The first section pertains to the specific elements, features, physical characteristics, functions, and various embodiments of the systems for producing ozonated water on demand and for reducing off-gassed ozone. The second section pertains to methods of using and making the described system as well as advantages associated with the described systems and methods. Although the described methods utilize one or more components of some embodiments of the described systems, other components, embodiments, methods, intended uses, etc. are contemplated and intended to be within the scope of the described systems and methods.

Producing Ozonated Water on Demand and for Reducing Off-Gassed Ozone

This application relates to systems and methods for producing ozonated water and for reducing off-gassed ozone. Specifically, this application discusses a system for producing ozonated water on demand. In other words, this application discusses a system for combining water and ozone and mixing the two in a manner that produces ozonated water without necessarily cycling the water through a circulation line to achieve a desired ozone concentration, or charge. Because the system does not require the ozonated water to be cycled and recycled through a circulation line to achieve and maintain a desired charge, the described systems need not discharge the ozonated water into a pressurized tank. Thus, the system can openly discharge the ozonated water after a single pass through the system. In addition, this application discusses an ozone destructor that renders off-gassed ozone harmless.

Figure 1:
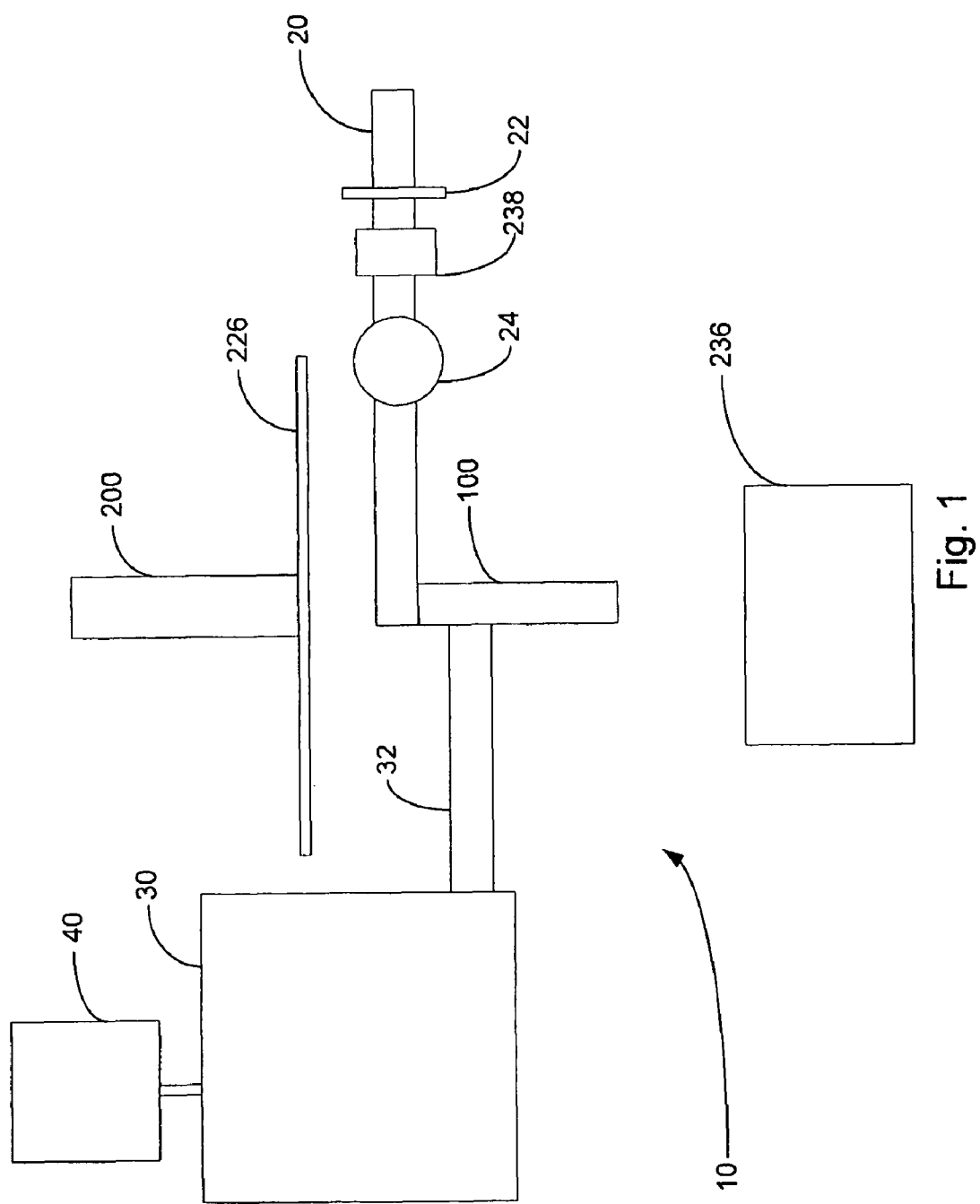
FIG. 1 illustrates some embodiments of a system for producing ozonated water on demand and for reducing off-gassed ozone.

Although the described system can comprise any component or device that is suitable for use with a system for producing ozonated water and/or reducing off-gassed ozone, FIG. 1 shows some embodiments of the system 10 for producing ozonated water on demand and reducing off-gassed ozone, wherein the system 10 comprises a water source (e.g., a water line 20), an ozone source (e.g., an ozone generator 30 and ozone line 32), a nozzle (e.g., an ozonated water on-demand nozzle 100), and an ozone destructor 200. To provide a better understanding of the system, a more detailed description of each of the aforementioned components is provided below.

As mentioned, the system can comprise a water source. The water source can be any water source that provides water suitable for the production of ozonated water, including a water source that is internal to (e.g., a water tank) or independent and external from the system (e.g., a municipal water source). For example, FIG. 1 illustrates the water source can comprise a water line 20 that is connected to an external water source.

The water source can have any component or characteristic suitable for use in the production of ozonated water. For example, FIG. 1 illustrates the water source (e.g., the water line 20) can comprise a water filter 22 and/or a valve 24 that controls the flow of the water and/or mixes the water with water of a different temperature (e.g., a hot and/or cold water tap).

The system can also comprise an ozone source. The ozone source can be any device or apparatus that is adapted to supply ozone gas to the system at a concentration sufficient for the production of ozonated water. For example, FIG. 1 shows the ozone source can be any known or novel ozone generator 30. Some non-limiting examples of suitable ozone generators can include generators that form ozone through a corona discharge, ultraviolet light, or cold plasma method. Additionally, while FIG. 1 shows the ozone source can comprise a single ozone generator 30, the system can comprise any suitable number of ozone generators.

In some preferred embodiments, the system comprises an ozone generator that forms ozone through the corona discharge method. In this method, concentrated oxygen can be provided by an oxygen source, such as an oxygen tank or the oxygen generator 40 shown in FIG. 1. The concentrated oxygen can then be delivered into the ozone generator 30, where an additional oxygen atom is temporarily bonded to the oxygen molecule, resulting in the formation of ozone. Stated differently, the ozone generator 30 produces or creates a temporary triatomic oxygen substance ($O_3$), or ozone, by adding an extra oxygen atom to the oxygen gas ($O_2$) from the oxygen source (e.g., oxygen generator 40).

The produced ozone is a natural cleaning agent. For instance, it has been determined that ozone is approximately 52% stronger than chlorine in getting rid of approximately 90% of the bacteria found on food. Additionally, the produced ozone tends to have a very short half-life compared to chemicals like chlorine. In fact, because the ozone is highly unstable, it almost immediately returns to its natural equilibrium or resting state of $O_2$ if allowed to do so.

The system can combine ozone and water to form an ozonated water solution in any manner that produces ozonated water with a desired ozone concentration in a single pass through the system. In other words, the system can mix the ozone and water in virtually any manner that does not require the ozonated water to be re-circulated through a circulation line to increase the ozone concentration in the solution. For example, FIG. 1 shows embodiments where the system 10 combines ozone from the ozone line 32 and water from the water line 20 together in an ozonated water on demand nozzle 100 to form ozonated water. Such a nozzle can comprise any nozzle capable of combining ozone and water to form a desired concentration of ozonated water in a single pass through the nozzle.

Figure 2:
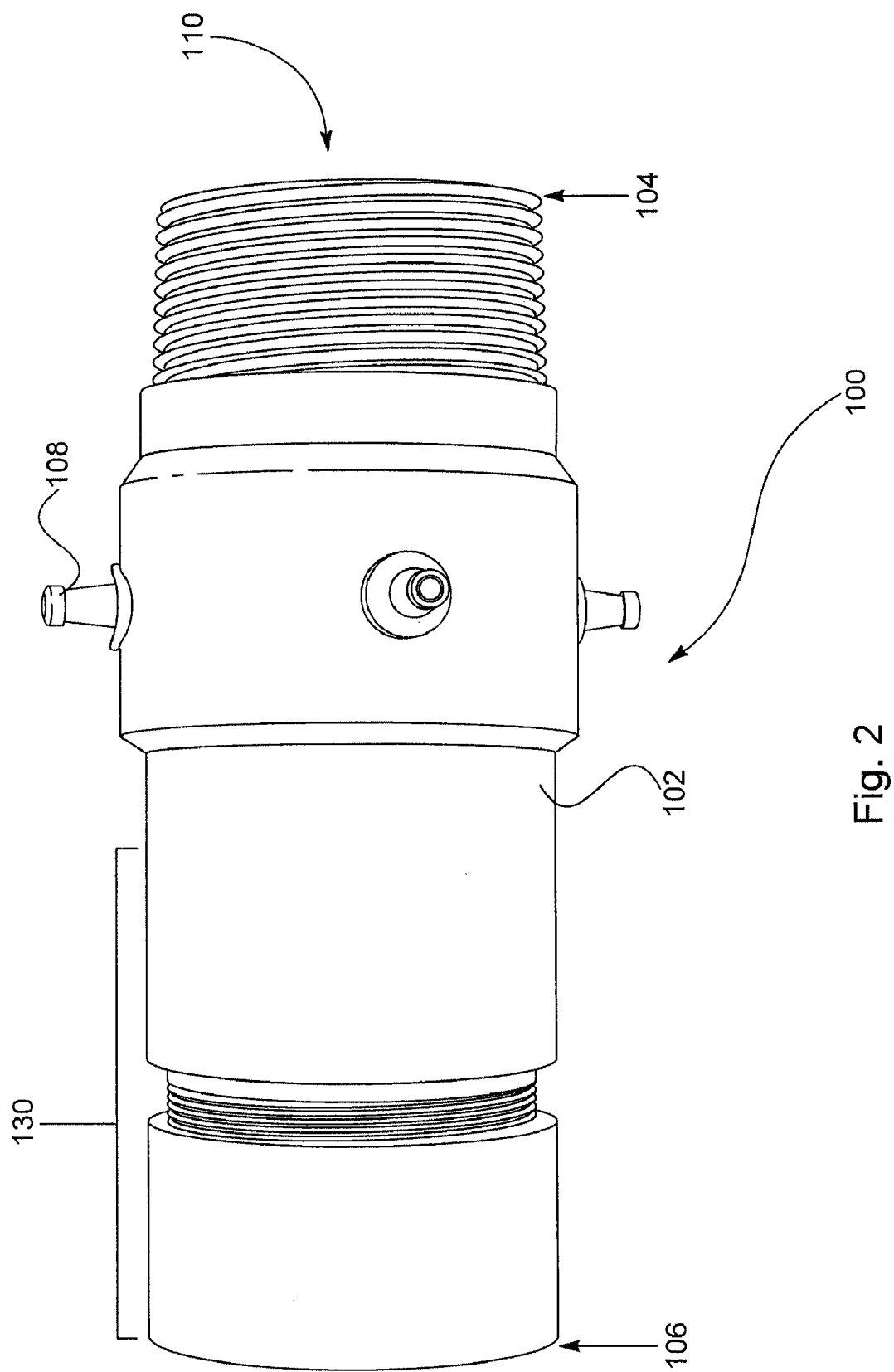
FIG. 2 illustrates a view of some embodiments of ozonated water on demand nozzle.
Figure 3:
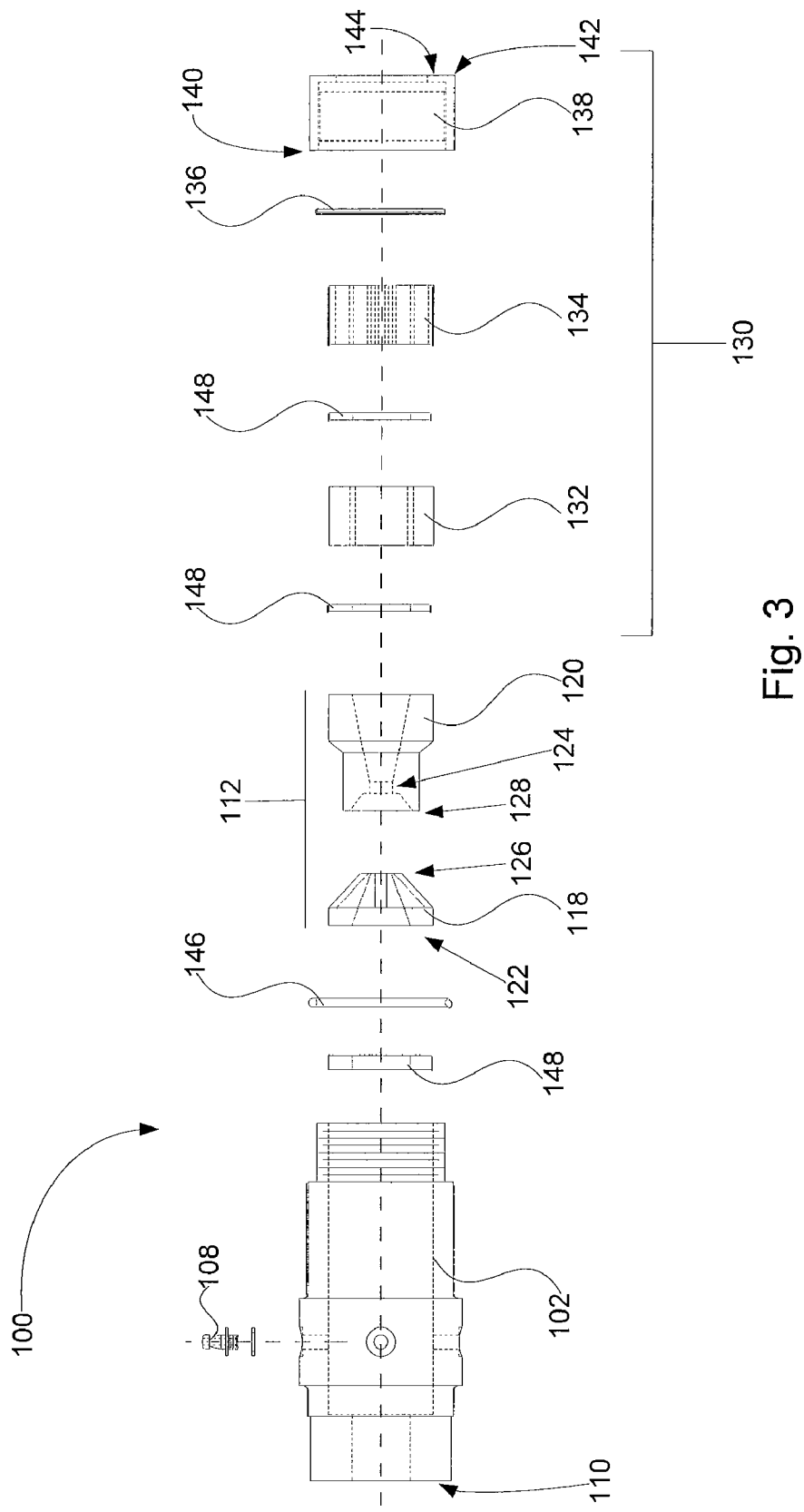
FIG. 3 illustrates an exploded view of some embodiments of the described nozzle.

Moreover, the nozzle can include any component that allows it to combine ozone and water to form highly concentrated, ozonated water in a single pass through the nozzle. For example, FIG. 2 shows some embodiments where the nozzle 100 comprises a body 102 with a first end 104 and a second end 106. FIG. 2 further shows the nozzle 100 can have multiple ozone inlet ports 108 and water inlet port 110. Additionally, FIG. 3 shows an exploded view of some embodiments of the nozzle 100, wherein the nozzle includes a venturi 112 and a single pass mixing mechanism 130.

As illustrated in FIG. 2, in some embodiments, water can enter through a water inlet Port 110 in the first end 104 of the nozzle 100, ozone can enter through the ozone inlet ports 108, the ozone and water can pass through the single pass mixing mechanism 130, and a high concentrate ozonated water solution can exit through the second end 106 of the nozzle 100. To provide a better understanding of the nozzle, the aforementioned components of the nozzle are described below in more detail.

Generally, the nozzle can comprise a body, which can have virtually any desired characteristic. For instance, the body can be any suitable size (e.g., length, diameter, height, width, etc.). Additionally, the body can be any suitable shape, including being substantially cylindrical, tubular, cuboidal, etc. For example, FIG. 2 shows the body 102 can be substantially cylindrical.

The nozzle comprises a water inlet port. In fact, the nozzle can have any suitable number of water inlet ports. By way of example, FIG. 2 shows some embodiments where the nozzle 100 comprises 1 water inlet port 110. However, in another example (not shown), the nozzle can comprise a plurality of water inlets.

The nozzle also comprises at least one ozone inlet port that allows ozone to enter the nozzle. Indeed, the nozzle can comprise any number of ozone inlet ports that improves the absorption of ozone into water. For instance, the nozzle can comprise as many as 200 ozone inlet ports or as few as 2. In one example, the nozzle comprises from about 2 to about 12 ozone inlets. In another example, the nozzle comprises from about 3 to about 6 ozone inlets. In still another example, FIG. 2 shows the nozzle 100 can comprise 4 ozone inlets ports 108 (the forth being out of view).

The water and ozone inlet ports can have any characteristic or configuration suitable for use with the nozzle. For example, the inlets can be any appropriate size or shape. Additionally, the inlets can be located in any suitable location on the nozzle. For example, FIG. 2 shows the ozone inlet ports 108 can be disposed in the side of the nozzle 100. The nozzle can also be adapted to be connected to the water source in any suitable manner. For example, FIG. 2 shows the first end 104 of the nozzle can be adapted to threadingly attach to the water line 20 of FIG. 1. Similarly, the ozone inlet port can be adapted to be connected the ozone source in any suitable manner. For example, FIG. 2 shows the ozone inlet ports 108 can be shaped so as to frictionally engage an ozone line 42 (shown in FIG. 1).

In some embodiments, the nozzle comprises a venturi. The venturi can be part of or separate from the nozzle body. Furthermore, the venturi can have any characteristic that permits water to flow through it in such a manner that ozone gas is drawn into the water. For example, the venturi can include a water passage that comprises a constriction and one or more ozone inlets channels. As water passes through the constriction in such a venturi, the velocity of water increases and the pressure of the water is caused to drop. Accordingly, the flow of water through the constriction can tend to draw ozone from the ozone source, through the ozone inlets in the venturi and into the water.

The venturi can include any number of pieces that allows it function as described. For example, the venturi can be a single-piece unit or, as shown in FIG. 3, the venturi 112 can comprise multiple pieces. Specifically, FIG. 3 shows some embodiments where the venturi 112 is divided into two pieces, the venturi nozzle 118 and the venturi diffuser 120. Although the venturi nozzle can serve many purposes, FIG. 3 shows some instances where a first end 122 of the venturi nozzle 118 serves to funnel water from the water inlet port 110 down to the constriction 124 in the venturi diffuser 120. Additionally, in some cases, a second end 126 of the venturi nozzle 118 is configured to fit in and abut the first end 128 of the venturi diffuser 120 so as to allow the ozone inlets (discussed below) to pass between the two. For example, FIG. 4*e* shows the venturi nozzle 118 can have grooves between its first end 122 and second end 126 that act as ozone inlets 116 when the venturi nozzle 118 is seated against the venturi diffuser 120.

The venturi can have any number of ozone inlets that allows the venturi to draw a sufficient amount of ozone into the water. In preferred embodiments, however, the venturi comprises a plurality of ozone inlets. For instance, the venturi can have from about 2 to about 200 inlets. However, in some instances, the venturi comprises from about 2 to about 10 inlets. In some preferred instances, the venturi comprises from about 4 to about 6 inlets. While not necessary, the venturi can have one ozone inlet for each corresponding inlet port of the nozzle. For example, a venturi used in a nozzle that has 4 ozone inlet ports can also comprise 4 corresponding ozone inlets, as is the case in FIG. 4*e*.

A plurality of inlets can be advantageous for several reasons. For instance, a plurality of inlets can mix the ozone and water better than a venturi with a single inlet. In one example showing the benefit of multiple inlets, a venturi with multiple inlets can be able to have smaller inlets without reducing the total amount of ozone that can be drawn into the venturi. Thus, such a venturi can produce smaller bubbles of ozone that provide increased ozone absorption over the larger bubbles that are typically produced by a venturi with a single inlet. In another example, a venturi with multiple inlets can be able to draw in and mix a larger amount of ozone, more efficiently, than can a venturi with a single inlet.

Additionally, the ozone inlets in the venturi can have any characteristic suitable to allow ozone to flow through them and into the water at a desired rate. For example, the ozone inlets can be any suitable size or shape that allows ozone to pass through the venturi and into the water.

After the water has passed through the venturi and the ozone has been drawn into the water, the system can be configured to mix the two in a manner that forms a highly concentrated, ozonated water solution in a single pass through the nozzle. For example, the nozzle can comprise a single pass mixing mechanism that mixes the water and ozone sufficiently so that the ozonated water that exits the nozzle has a desired ozone concentration. Additionally, while the single pass mixing mechanism 130 can be incorporated into the nozzle 100, as is illustrated in FIG. 3, in other embodiments, the mixing mechanism need not be directly attached to the nozzle.

After a single pass through the nozzle and/or mixing mechanism, the ozonated water can have any suitable concentration of ozone. For example, the ozonated water can have an ozone concentration between about 0.01 parts per million ("ppm") and about 50 ppm. In another example, the ozonated water produced can have an ozone concentration between about 1 and about 10 ppm. Indeed, in a preferred example, the ozonated water produced by the system can have a concentration between about 1.5 ppm and about 5 ppm.

The mixing mechanism can have any component or characteristic that allows it to mix ozone and water to form ozonated water with a suitable ozone concentration in a single pass through the mixing mechanism. FIG. 3 illustrates that, in some embodiments, the mixing mechanism 130 can comprise one or more helical mixers 132, laminators 134, meshes 136, and/or injector caps 138; each of which is respectively discussed below.

In some embodiments, the mixing mechanism comprises a helical mixer. Such a helical mixer can serve many purposes, including causing the ozone and water to be swirled and form a vortex as they pass through the helical mixer. Accordingly, the helical mixer can cause improved mixing and ozone absorption within the water. Although the helical mixer can have any characteristic that allows it to cause the water and ozone to swirl and mix, FIGS. 3, 5i, and 5j show that, in some cases, the helical mixer 132 can have a ring-like shape. In such cases, the internal surface of the helical mixer can be configured to cause the solution to swirl. For example, the inner surface of the helical mixer can have helical grooves or ridges that cause the solution to swirl.

In some circumstances, the mixing mechanism comprises a laminator. The laminator can serve several purposes, such as further increasing the mixing of the water and ozone by channeling the water as it passes through the laminator. The laminator can have any characteristic that allows it to channel the ozonated water as the solution passes through the laminator. For example, FIGS. 3, 5d, 5e, and 5f show some embodiments of the laminator 134 that comprise a plurality of holes passing through it. Even though the laminator 134 can have any number of holes, with any suitable characteristic, FIG. 5d show implementations where the laminator 134 comprises 6 circular holes that run substantially parallel with the length of the nozzle body. Although the inner surfaces of the laminator can be configured to cause the solution to swirl, in other instances, the inner surfaces of the laminator can be smooth.

FIG. 3 shows that, in some embodiments, the mixing mechanism 130 comprises at least one mesh 136. This mesh can serve many purposes, including reducing the size of the ozone bubbles to increase the surface area of the ozone gas within the water and causing the water and ozone mixture to be further mixed. The mesh can comprise any characteristic known to meshes that is appropriate for use with ozonated water and can increase mixing. For example, the mesh can have any suitable screen mesh size known in the art. In another example, FIG. 3 shows the mesh can comprise a single layer of mesh 136 that is disposed substantially perpendicular to the length of the nozzle body 102. Nevertheless, in other embodiments, the mixing mechanism can comprise a plurality of mesh layers. For example, the mixing mechanism can comprise from about 2 to about 200 mesh layers. In another example, the mixing mechanism can comprise between about 3 and about 12 mesh layers. In still another example, the mixing mechanism can comprise from about 4 to about 8 mesh layers. In some preferred embodiments, however, the mixing mechanism comprises about 6 mesh layers. In each of the aforementioned examples concerning a plurality of mesh layers, each mesh layer can be separated from another layer by any desired distance, including, but not limited to, $\frac{1}{64}$, $\frac{1}{8}$, $\frac{1}{4}$, $\frac{1}{2}$, or 1 inch. However, in yet other embodiments, the layers of mesh need not be evenly separated and/or disposed perpendicular to the nozzle body. For instance, the mesh can be wadded or folded within the mixing mechanism as desired.

According to some implementations, the mixing mechanism comprises an injector cap. The injector cap can serve many purposes, such as holding components (e.g., the laminator, the helical mixer, and/or the mesh) within the mixing mechanism and channeling the ozonated water as it exits the mixer. The injector cap can channel the ozonated water in virtually any desired manner, including as a stream, a mist, a spray, etc. The injector cap can comprise any characteristic suitable for achieving its intended purposes. For example, FIG. 3 shows the injector cap 138 can comprise a hollow sleeve with a first end 142 that is connectable to the nozzle body 102 and a second end 142 that comprises a lip 144. In such embodiments, the lip both serves to channel the ozonated water and to retain other components within the mixing mechanism.

In addition to the aforementioned components, the nozzle and/or mixing mechanism can comprise virtually any other component or characteristic that improves the function of the mixing mechanism and/or nozzle. For example, the inner surface of the venturi diffuser can comprise grooves, veins, indentations, ridges, or protuberances that act to increase mixing or swirling of the ozone and water. In another example, the mixing mechanism can comprise one or more balls. In such instances, the ozone and water can be forced to flow around the balls in a manner that causes increased mixing of the ozone and water. In still another example, the nozzle and/or mixing mechanism can comprise one or more o-rings, seals, and/or gaskets. For instance, FIG. 3 illustrates some embodiments where the nozzle 100 and mixing mechanism comprise an o-ring 146 and seals 148.

Even though nozzle and mixing mechanism have proven useful for mixing ozone and water in a single pass through system, the system is also capable of incorporating other known materials (e.g., sanitizing agents, disinfecting agents, antibiotics, etc.) into the ozonated water solution. In fact, sanitizing and disinfectant agents can actually be safer when used with the system because the agents can be metered for exact dilution and the amount of handling the dangerous cleaning agents by a user can be reduced. These additional agents can be added to the ozonated water solution in any suitable manner, including by being added to the water source, the ozone source, or by being added separately.

Due to the hazardous nature of ozone, in some embodiments, the system can comprise an ozone destructor. The ozone destructor can receive air containing ozone, ozonated water vapor, and/or water vapor, and cause them to return to their natural resting state of equilibrium as oxygen ($O_2$) and/or water ($H_2O$).

Figure 6:
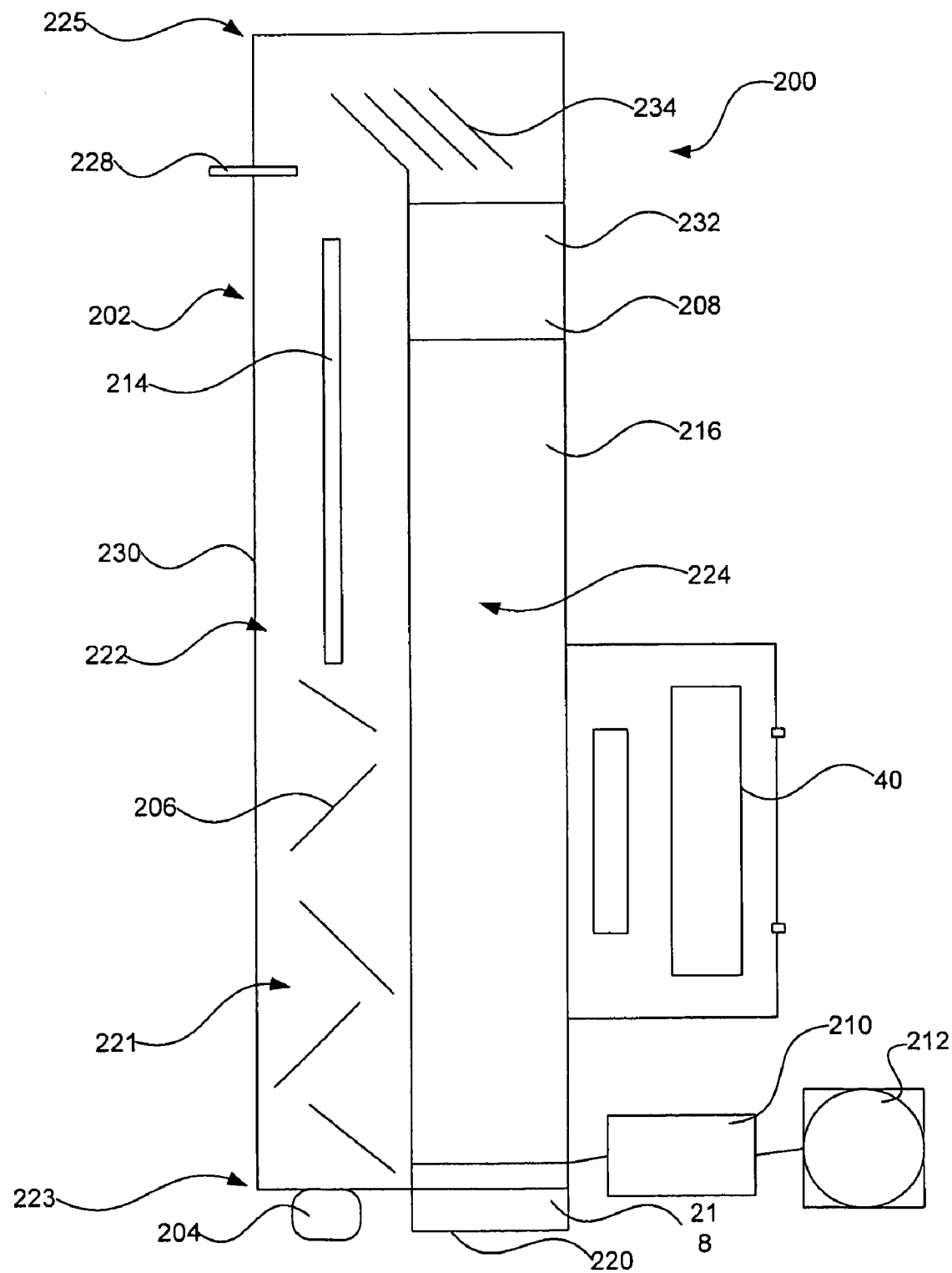
FIG. 6 illustrates some embodiments of the described ozone destructor.

The ozone destructor can comprise any component that allows it to accomplish its intended purposes. For example, FIG. 6 shows the destructor 200 can comprise a housing 202 and one or more air inlets 204, drying mechanisms (e.g., a demisting vein 206, a desiccant 208 and 210, and/or a chiller 212), ozone reducing mechanisms (e.g., a heater rod 214 and a catalyst 216), ventilating mechanisms 218 (e.g., fan 218), and/or air outlets 220.

As mentioned, the destructor can comprise a housing. The housing can have any characteristic suitable for use in an ozone destructor. For example, the housing can be any shape, including, but not limited to, cylindrical, elongated cuboidal, rectangular, tubular, irregular, and so forth. For example, FIG. 6 shows a cross sectional view of the destructor 200 where the housing 202 is substantially tubular. Additionally, the housing can be any suitable size (e.g., length, width, height, diameter, etc.). Accordingly, the destructor can be adapted to a variety of applications, which require different amounts of air to be passed through the destructor.

The housing can define an air passage duct 221. The air passage duct can have any characteristic suitable for use in an ozone destructor. For instance, the housing can define a plurality of chambers. By way of non-limiting example, FIG. 6 shows the housing 202 can comprise at least 2 chambers, a first 222 and a second chamber 224. The multiple chambers can perform several functions, including allowing the air and ozone to be incrementally dried and reduced, respectively, as they pass through the various chambers.

Where the housing has multiple chambers, the various chambers can be connected to each other with any suitable relation. For example, although the first and second chamber can be connected end to end so that the housing has a length that is substantially equal to the length of the two chambers, end to end. However, in preferred embodiments, one or more of the chambers is offset to one side another chamber so that the length of the housing is approximately the length of the longest chamber. For example, the first and the second chamber can run at an angle to, be perpendicular to, or be parallel with each other. For instance, FIG. 6 shows some embodiments where the first chamber is offset to one side of the second chamber, and the two chambers run substantially parallel with each other. As illustrated in FIG. 6, the first chamber 222 extends from a first end 223 to a second end 225 where the duct is bent at about a 180 degree angle so that the duct continues to extend from the first end 225 of the second chamber 224 to its second end 225. As shown in this example, the ozone destructor can comprise an air passage duct that is approximately twice the length of a single chamber, while the length of the housing remains approximately the length of one chamber. This increased length can better allow the destructor to dry and reduce the air and ozone, while providing room for additional components that do not typically fit within a conventional destructor.

In some implementations, the destructor comprises an air inlet through which air containing ozone, ozonated, water vapor, or water vapor can enter the destructor. The air inlet can have any characteristic that allows it to receive ozonated air and/or water vapor from a source that releases ozone. For example, the air inlet can be any suitable size. For instance, the air inlet can have a diameter as small as 1/64 of an inch or as large as 20 feet. However, in preferred embodiments the air inlet has a diameter between about 1 and about 6 inches. Indeed, in some embodiments, the air inlet has a diameter of about 2 inches. In another example, the air inlet can be adapted to be connected to an apparatus that channels air to the air inlet. For example, the air inlet can be adapted to be connected to a hose that channels air containing ozone from an ozone source, such as an ozone generator or a tank containing ozonated water. In another example, the air inlet can be adapted to be connected to vent hood 226 (as shown in FIG. 1) that channels ambient air into the air inlet.

In some embodiments, the destructor can comprise one or more mechanisms for drying the air. By acting to dry the air, the drying mechanisms can allow the ozone in the air and/or ozonated water vapor to be reduced more easily. Additionally, because dry air can increase the efficiency of an ozone generator using the dry air, in some embodiments, the drying mechanism is used by the ozone generator to generate ozone. In order to dry the air, the destructor can comprise any known or novel drying mechanism suitable for use in an ozone destructor. According to some embodiments, FIG. 6 shows that some examples of suitable drying mechanisms can include demisting veins 206, a desiccant 208 and 210, and a chiller 212.

Where the destructor comprises one or more demisting veins, the demisting veins can be located in any suitable location or with any suitable orientation and/or configuration in the destructor that allows them to reduce moisture in the air that passes through the destructor. For example, FIG. 6 shows the demisting veins 206 can be disposed near the air inlet 204 so that as air enters the air passage duct 221, the air is caused to move past the demisting veins 206. Additionally, FIG. 6 shows some embodiments where the veins 206 are oriented so as to be in a zig-zagged configuration. In such embodiments, the zig-zagged configuration can cause the air to be directed into contact with another vein and can further allow water vapor to condense on the veins and/or to drip back towards the air inlet.

The demisting veins can also have any characteristic that allows them to reduce the moisture content of the air that passes through the destructor. In one example, the demisting veins have a rough or a smooth surface, are made of a material that has a specific heat conducive to condensing water vapor or water mist, or are otherwise configured to collect moisture. In another example, the demisting veins are chilled or refrigerated to collect water. For instance, chilled demisting veins may act to collect and freeze moisture. In such instances, the water may be removed from the veins in any suitable manner, including by defrosting the veins.

In some embodiments, the drying mechanism can comprise a desiccant that absorbs moisture from the air. Although the destructor can comprise any suitable desiccant, some non-limiting examples of suitable desiccants can include a molecular sieve desiccant, a montmorillonite clay desiccant, a silica gel desiccant, an activated alumina desiccant, a calcium oxide desiccant, and/or a calcium sulfate desiccant. FIG. 6 illustrates that, in some embodiments, an activated alumina desiccant 208 and a molecular sieve desiccant 210, such as a porous crystalline aluminosilicate, can be used to remove moisture from the air passing though the destructor 200.

In some instances, the drying mechanism can comprise a chiller. In such instances, the chiller can serve to pull moisture from the air as the air is refrigerated. Additionally, where the destructor comprises a heating mechanism (described below), the chiller can also serve to lower the temperature of the heated air before it is exhausted from the destructor. To accomplish the intended purposes, any suitable chiller known in the art can be used with the destructor. For example, FIG. 6 shows embodiments where the destructor 200 can comprise a ¼" copper coil with a chiller 212. In such embodiments, some of the water moisture in the air passing through the destructor can condense on the coils of the chiller. FIG. 6 also shows the condensed water from the chiller can be absorbed by a desiccant (e.g., the activated alumina desiccant 208).

The destructor can comprise one or more mechanisms for reducing ozone to oxygen. Indeed, the destructor can comprise any known or novel mechanism for reducing ozone, including, but not limited to, a heating mechanism and/or a catalyst for reducing ozone to oxygen.

Where the reducing mechanism comprises a heating mechanism, the destructor can comprise any known or novel heating mechanism suitable for reducing ozone to oxygen. Some non-limiting examples of suitable heating mechanisms can comprise a heater rod, heater plate, heater coil, etc. For instance, FIG. 6 shows some embodiments where the destructor 200 comprises a heater rod 214. Additionally, the heating mechanism can be controlled in a variety of manners, including, but not limited to, the use of a manual switch or a temperature controlled switch. For example, FIG. 6 shows some embodiments where the heater rod 214 is controlled by the temperature controlled switch 228.

Where the reducing mechanism comprises a catalyst, the destructor can use any suitable catalyst that can reduce ozone to its natural state of equilibrium as oxygen. Some non-limiting examples of such catalysts can include manganese oxide, manganese dioxide-copper oxide, vanadium oxide, and/or magnesium oxide. In some preferred embodiments, the catalyst can comprise a manganese dioxide catalyst, such as CARULITE® produced by CARUS CO.®.

Although the heating mechanism and catalyst can be used separately, FIG. 6 illustrates some embodiments where the destructor 200 comprises both a heating rod 214 and catalyst 216. Such embodiments can be more efficient at reducing ozone than can embodiments that comprise only one or the other. As a result, embodiments that comprise both a heating mechanism and a catalyst can be preferred where a high volume of air passes through the destructor.

In some embodiments, the destructor can optionally comprise a ventilation mechanism that acts to pull or push air through the air duct. Thus, a ventilation mechanism can greatly increase the amount of air that passes through the destructor. Any conventional mechanism that serves to pull or push air through the air duct and is suitable for use with an ozone destructor can be used to increase air flow. For example, FIG. 6 shows a fan 218 can be used to increase air flow through the destructor 200.

The ventilation mechanism can have any characteristic suitable for use with the described destructor. For example, the ventilating mechanism can be of any suitable size or speed. Because the catalyst can more efficiently reduce ozone when air is moved at an optimal range of speeds, it can be beneficial to have the ventilation air move within the optimal range of speeds. In one example, it can be beneficial to have the air between about 2 feet per second and at about 1 foot per second along the length of the catalyst. Accordingly, the ventilating mechanism can be adapted to move air through the destructor at a suitable rate. In one example of a suitable rate, the ventilating mechanism can move air through the destructor at between about 1 and about 1,000 cubic feet per minute ("CFPM") or more. In another example, the ventilating mechanism can be adapted to create an air flow of up to about 100 cfpm. Indeed, FIG. 6 shows that, in some embodiments, the fan 218 can move air through the destructor 200 at about 60 cfpm±10 cfpm.

After air passes through the destructor, the air can be exhausted from the destructor through one or more air outlets. In some cases, the air is exhausted to atmosphere. However, in other cases, because the air has been thoroughly dried, the air can be exhausted into an air intake of an oxygen or ozone generator. In still other cases, FIG. 6 shows that air can exit to atmosphere (e.g., through the air outlet 220) or air can exit to the ozone generator 40.

In addition to the previously mentioned components, the destructor can comprise any other component that is suitable for use with the described destructor. In one example, the destructor can comprise an air filter (not shown) that is disposed near the air inlet to remove dust and debris from the air. In another example, FIG. 6 shows that where the destructor comprises a heating mechanism, the destructor 200 can comprise an insulation jacket 230. The insulation jacket can help maintain the desired temperature in the destructor as well as to reduce the temperature of the outside of the destructor. In still another example, FIG. 6 illustrates that the destructor 200 can comprise an inspection window 232. Such a window can be useful for monitoring the desiccant and determining whether the desiccant should be replaced. In yet another example, FIG. 6 shows the destructor 200 can comprise one or more air deflectors 234 to direct the air from the first chamber 222 to the second chamber 224.

While the ozone destructor can be particularly useful with the described system, the ozone destructor need not be used in conjunction with the system. In fact, the ozone destructor can be used with any suitable system, device, method, etc. that releases ozone and/or ozonated water vapor. For example, the ozone destructor can be used in conjunction with conventional systems for producing ozonated water, ozone generators, drains, recipients (e.g., the wash basin 236 in FIG. 1, a swimming pool, ice maker, sink, wash basin, cistern, etc.), and so forth that can be associated with ozonated water.

Associated Methods and Advantages

Figure 7:
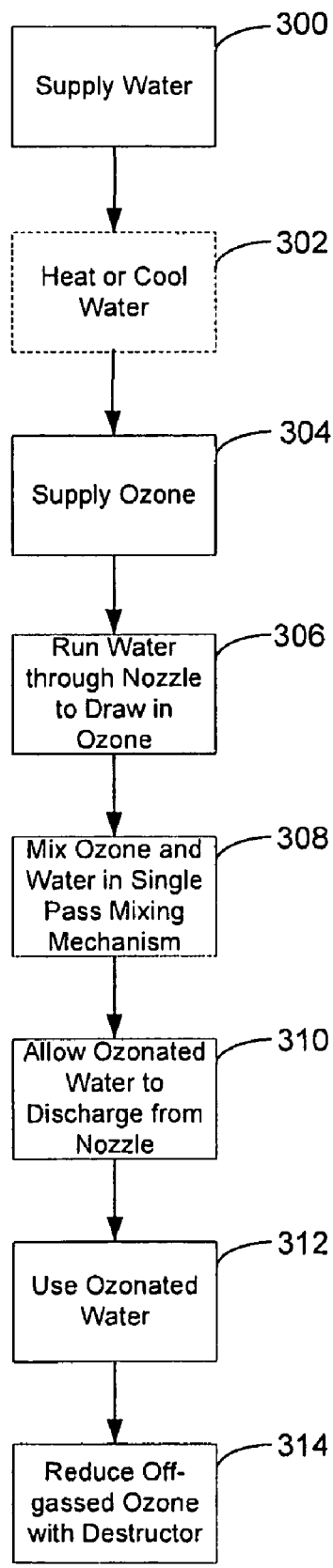
FIG. 7 depicts some embodiments of a method for using the system for producing ozone-on-demand and for reducing off-gassed ozone.

Although the system can be used in any suitable manner, a non-limiting example of how it can be used is given herein. Specifically, FIG. 7 shows that, according to some embodiments, use of the system begins at 300 by supplying water to the nozzle. As discussed earlier, the water can be provided from any suitable source.

At 302, FIG. 7 shows the water can optionally be heated or cooled. Because ozone concentrations can be higher in colder water, in some circumstances, it can be beneficial to cool the water to a low temperature (e.g. between about 33 and about 45 degrees Fahrenheit). Although ozone concentration can be reduced as the temperature of the water increases, in some instances, higher temperatures (e.g., between about 88 and about 112 degrees Fahrenheit or between about 112 and about 220 degrees Fahrenheit) can be actually be preferred. For example, U.S. patent application Ser. No. 10/306,168, entitled "Method and Device for Providing Ozone Sanitation of Various Objects" discusses using ozonated water at higher temperatures to rehydrate food items. Indeed, the temperature of the water and/or ozonated water solution can be varied as desired while using the system. For example the water can be heated or cooled, before, during, and/or after it is ozonated. By way of example, FIG. 1 shows the water line can comprise a heater and/or cooler 238.

At 304, FIG. 7 shows the method can continue by supplying ozone to the nozzle. Then, 306 shows the movement of water through the venturi can act to draw ozone into the water. Because the nozzle allows ozone to be mixed with water to form a high concentrate ozonated water in a single pass through the nozzle (shown at 308), a constant supply of ozone need not be supplied to the nozzle. Instead, ozone can be supplied to the nozzle when desired. For instance, non-ozonated water can run from the nozzle to rinse dirt or other debris from an object. Then, when desired, ozone can be supplied to the nozzle and ozonated water can be produced for another desired purpose, such as sanitizing an object.

Because the nozzle allows the ozonated water to have a high concentration of ozone without being stored in a pressurized tank and being re-cycled through a circulation loop, FIG. 7 at 310 shows the ozonated water can be openly discharged from the nozzle. For instance, water and ozone can enter the nozzle and ozonated water can be discharged directly from the nozzle on to an object to sanitize the object. Finally, at 314, FIG. 7 shows that any ozone that is off gassed from the ozonated water solution can be rendered harmless by the ozone destructor.

Figure 8:
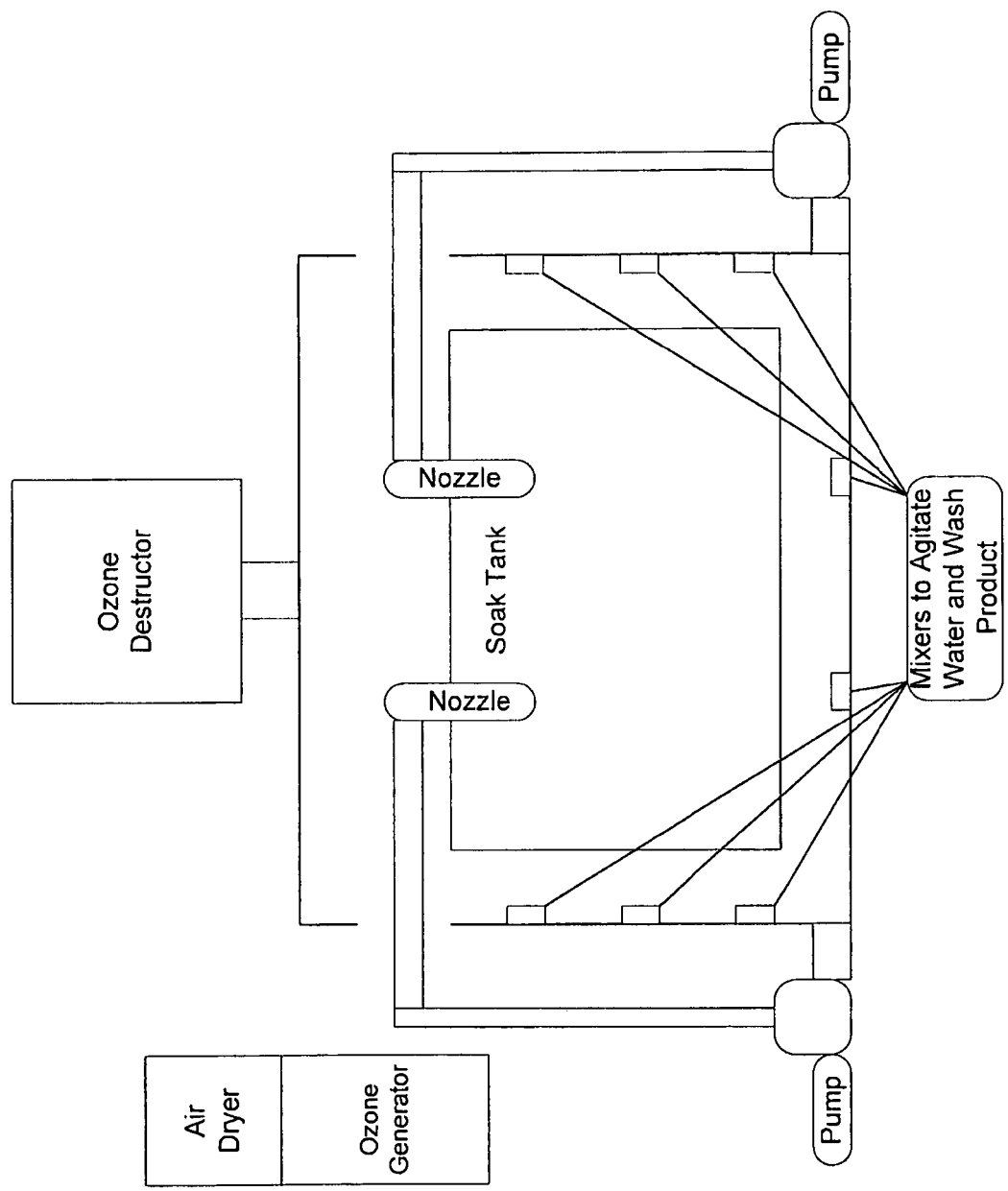
FIGS. 8-12 illustrate different applications for some embodiments of the system for producing ozonated water on demand and for reducing off-gassed ozone.
Figure 9:
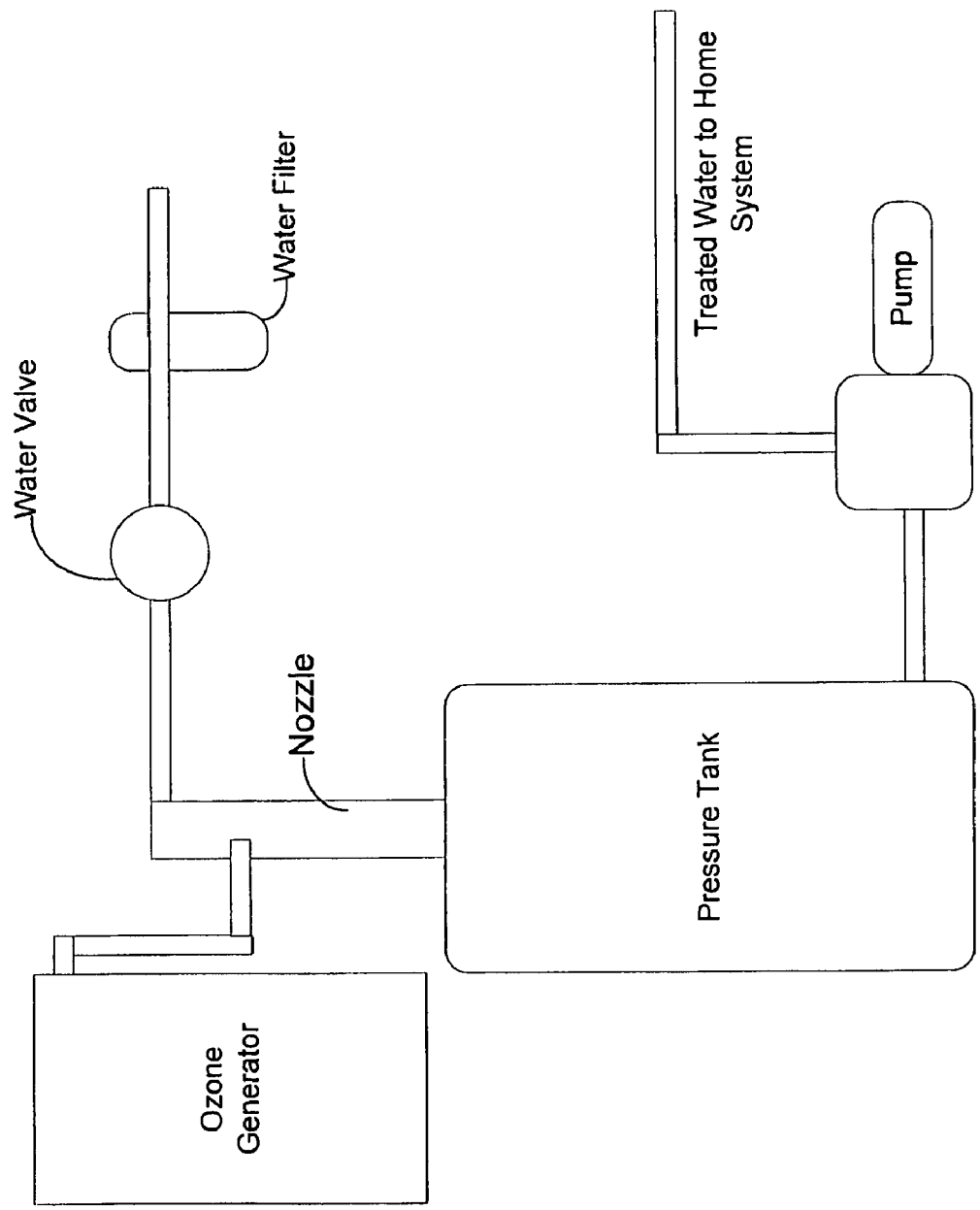
Figure 10:
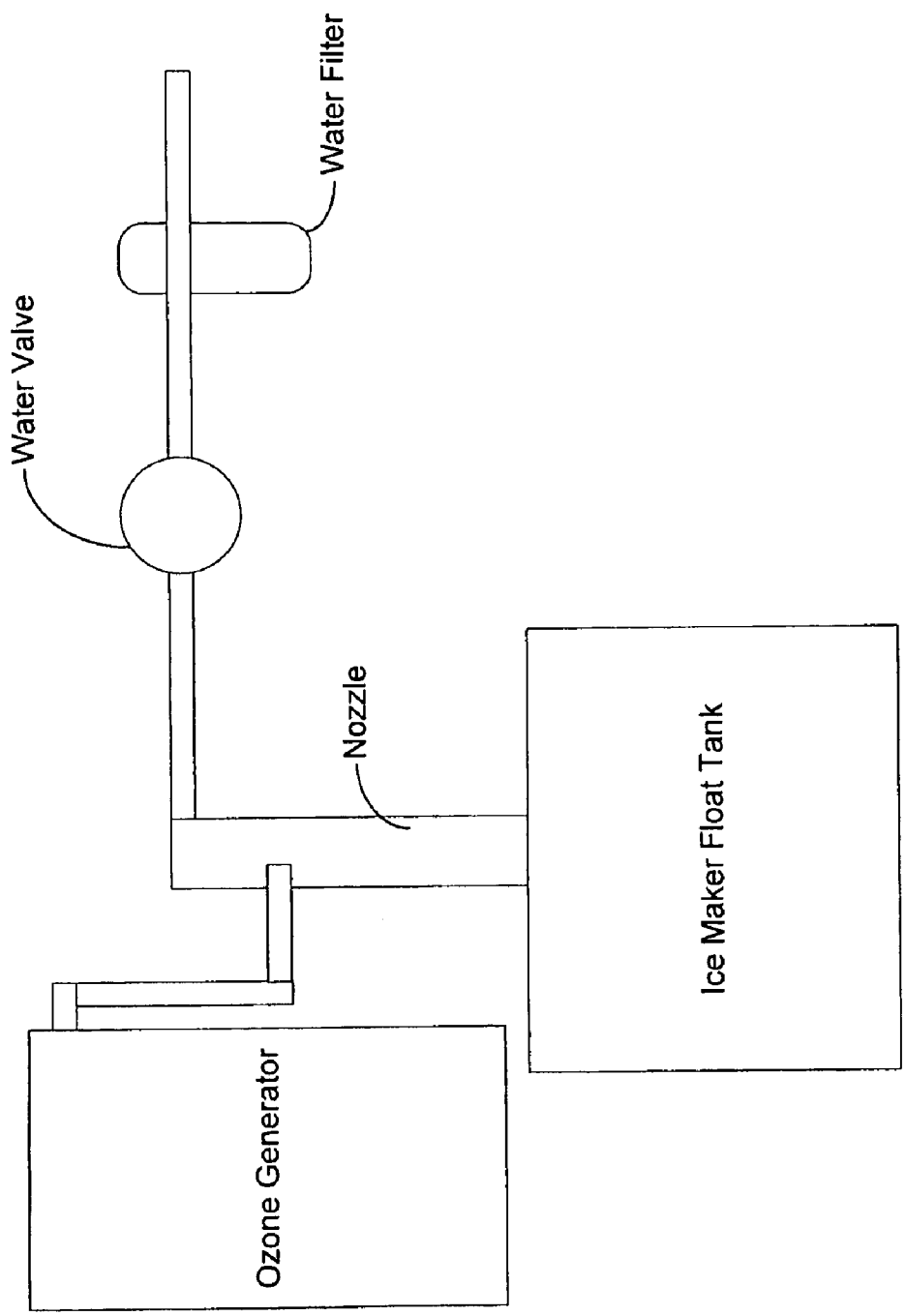
Figure 11:
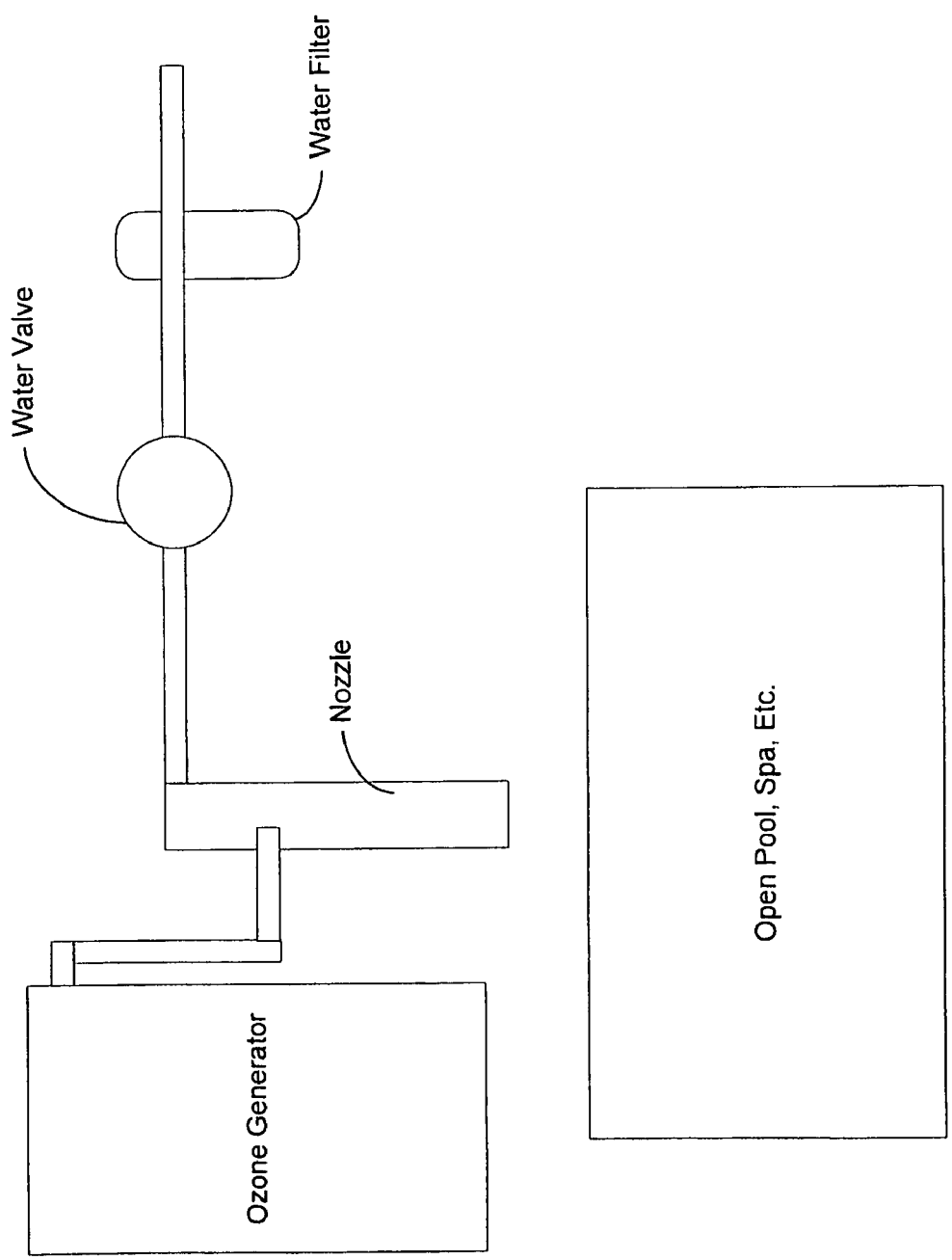

While the system can be used for practically any application that involves ozonated water, FIGS. 8-10 illustrate some typical applications. For example, FIG. 8 shows some embodiments where multiple nozzles are used to openly discharge ozonated water into an industrial ozone soak tank with assisted mixers to aid in washing and sanitizing. In another example, FIG. 9 illustrates a representative embodiment in which the system is used to sanitize water for residential use. In still another example, FIG. 10 shows a representative embodiment in which the system is used to sanitize water for the making of ice. In a yet another example, FIG. 11 shows the system can be configured to openly discharge ozonated water into a recipient, such as a pool or spa. Finally, FIG. 12 shows a representative embodiment of the system used in conjunction with a water chill tank.

Figure 12:
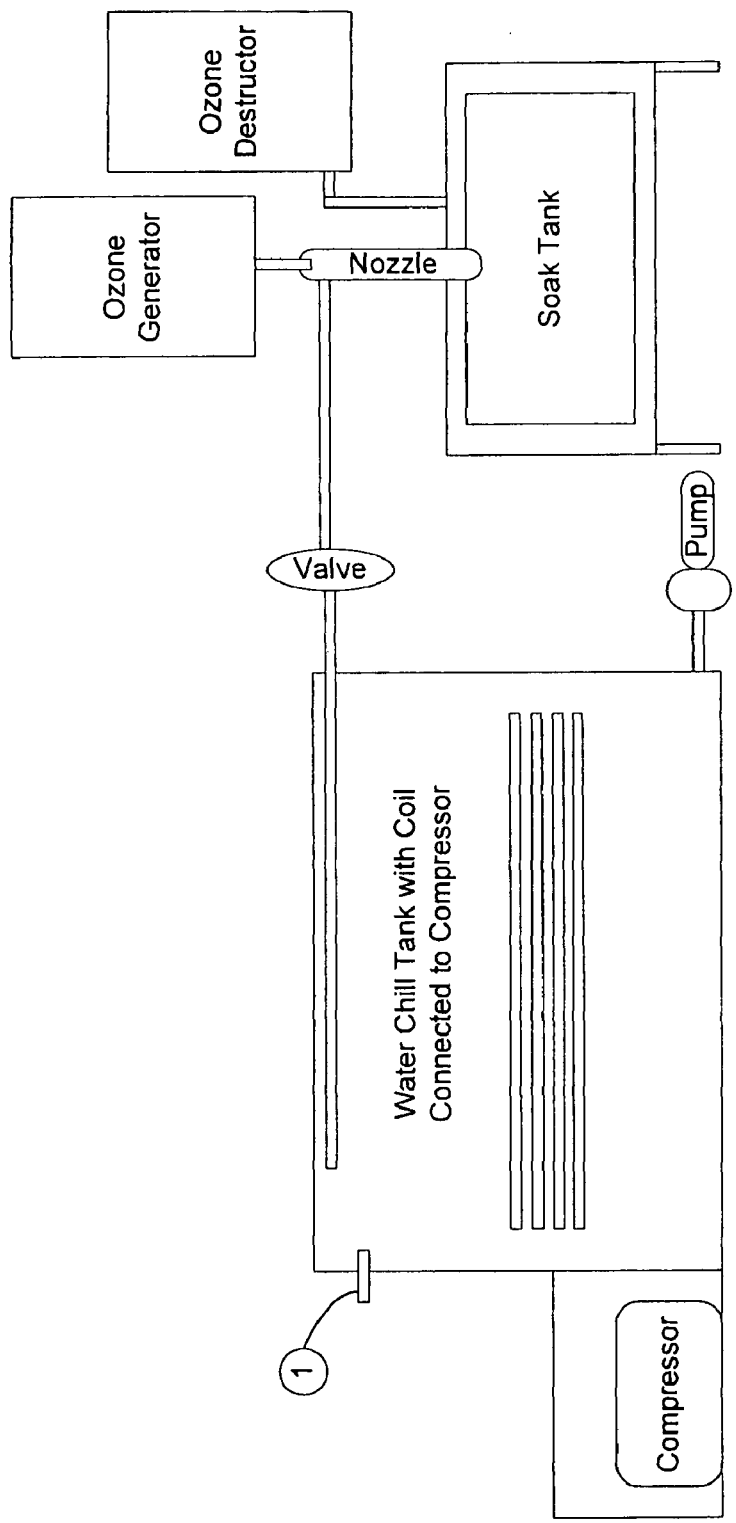

Specifically, FIG. 12 shows the system comprises a float valve no. 1 through which water enters the water chill tank. Additionally, FIG. 12 shows the system comprises a refrigeration compressor, which is connected to a cooling coil, and a pump, which is configured to circulate and re-circulate water past the coils and/or to a separate soak tank. As shown, a valve, in combination with the pump, directs water from the chill tank to the nozzle. At the nozzle, ozone from the ozone generator is mixed with the water to form ozonated water. In turn, FIG. 12 shows the nozzle feeds the ozonated water into the soak tank, where an objected can be washed and disinfected. Finally, FIG. 12 shows that off-gassed ozone can be reduced by the ozone destructor.

The various components of the system (e.g., the nozzle and destructor) can be constructed from any material suitable for use with ozone, ozonated water, and ozonated water vapor. Some non-limiting examples of suitable materials can include a metal, a metal alloy (e.g., stainless steel), a polymer, an elastomeric material, a rubber, a plastic, polyvinyl chloride, a ceramic, composites, and combinations thereof. Additionally, the various components of the system can be made in any suitable manner, including but not limited to methods involving extrusion, stamping, etching, molding, cutting, etc.

The described systems and methods can provide several advantages over conventional methods. For example, because the ozonated water can be produced in a single pass through the nozzle, the nozzle can save time over conventional systems that require the ozonated water to be re-circulated through a circulation loop. Additionally, because the described system does not require a recirculation loop and/or a pressurized tank, the described system can be less expensive and require less room. Moreover, in some cases, the described system can provide a higher concentration of ozone in the ozonated water than other systems.

The described destructor can also provide several advantages over conventional ozone destructors. For example, because the destructor can have multiple chambers, the destructor can progressively dry the air and reduce ozone. Accordingly, the destructor can be more effective than some conventional ozone destructors.

Additionally, because the destructor can have a relatively large air intake and/or a ventilation mechanism, the destructor can be able to dry and reduce a larger amount of air and ozone than some conventional destructors. Moreover, because the first chamber of the destructor can be offset to one side of the second chamber, the destructor does not require much more room than a conventional ozone destructor.

The present invention can be embodied in other specific forms without departing from its spirit or essential characteristics. Moreover, the described embodiments are to be considered, in all respects, only illustrative and not restrictive. As such, the scope of the invention is indicated by the appended claims, rather than by the foregoing description. All changes that come within the meaning and range of equivalency of the claims are to be embraced within their scope.

What is claimed and desired to be secured is:

1. A nozzle for producing ozonated water on demand, comprising:
   a nozzle body that is adapted to be connected to a water source and an ozone source;
   a venturi that is adapted to allow water to flow through it in a manner that draws ozone into the water; and
   a single pass mixing mechanism that is adapted to mix ozone with water to form a highly concentrated, ozonated water solution in a single pass through the mixing mechanism, wherein the mixing mechanism comprises a helical mixer with a substantially straight bore having an internal surface shaped to cause the ozone and water to mix, and wherein the mixing mechanism further comprises a laminator that includes a plurality of holes that run substantially parallel to a longitudinal axis of a longest length of the nozzle body.

2. The nozzle of claim 1, wherein the venturi comprises multiple ozone inlets.

3. The nozzle of claim 1, wherein the nozzle is adapted to openly discharge the ozonated water solution.

4. The nozzle of claim 1, wherein the mixing mechanism comprises at least one mesh adapted to break ozone bubbles into smaller bubbles.

5. The nozzle of claim 4, wherein the mixing mechanism comprises two or more layers of mesh.

6. The nozzle of claim 1, wherein the nozzle comprises a water inlet at its first end and an ozonated water outlet at its second end, which is substantially opposite to the first end, and wherein the mixing mechanism is adapted to release the ozonated water solution from the ozonated water outlet at a concentration between about 1 ppm to about 10 ppm after a single pass directly through the mixing mechanism.

7. The nozzle of claim 1, wherein the nozzle is adapted to produce ozonated water with an ozone concentration between about 1 ppm and about 10 ppm.

8. A system for producing ozonated water on demand, the system comprising:
   a water source;
   an ozone source; and
   a nozzle comprising:
      at least one water inlet port that is adapted to receive water from the water source;

at least one ozone inlet that is adapted to receive ozone from the ozone source;

a venturi that is adapted to allow the water to flow through it in a manner that draws the ozone into the water; and a single pass mixing mechanism that is adapted to mix the ozone with the water to form a high concentrate, ozonated water solution in a single pass through the mixing mechanism, wherein the mixing mechanism comprises a laminator that includes a plurality of holes that run substantially parallel to a longitudinal axis of a longest length of the nozzle body, and wherein the mixing mechanism further comprises a helical mixer having a ring-like shape with an internal feature that is shaped to cause the ozone and the water to swirl and mix.

9. The system of claim 8, wherein the venturi comprises multiple ozone inlets.

10. The system of claim 8, wherein the nozzle is adapted to receive water at a first nozzle end and to openly discharge the high concentrate, ozonated water solution at a second nozzle end, disposed opposite to the first nozzle end.

11. The system of claim 8, wherein the nozzle is adapted to produce ozonated water with an ozone concentration selected from:
  (a) about 0.01 ppm to about 50 ppm:
  (b) about 1 ppm and about 10 ppm; and
  (c) about 1.5 ppm and about 5 ppm.

12. The system of claim 8, wherein the mixing mechanism comprises at least one mesh adapted to break ozone bubbles into smaller bubbles.

13. The system of claim 12, wherein the mixing mechanism further comprises multiple layers of mesh.

14. A nozzle for producing ozonated water on demand, comprising:

a nozzle body adapted to be connected to a water source and an ozone source;

a venturi adapted to allow water to flow through it in a manner that draws ozone into the water; and a single pass mixing mechanism that is adapted to mix ozone with water to form a highly concentrated, ozonated water solution in a single pass through the mixing mechanism, wherein the mixing mechanism comprises a helical mixer with a substantially straight bore having an internal feature shaped to cause the ozone and water to mix, wherein the mixing mechanism further comprises a laminator that includes a plurality of holes that run substantially parallel to a longitudinal axis of a longest length of the nozzle body;

wherein the nozzle comprises a water inlet at its first end and an ozonated water outlet at its second end, which is opposite to the first end; and wherein the helical mixer and the laminator are disposed between the venturi and the ozonated water outlet.

15. The nozzle of claim 14, wherein the mixing mechanism is adapted to release the ozonated water solution from the ozonated water outlet at a concentration between about 1 ppm to about 10 ppm after a single pass directly through the nozzle.

16. The nozzle of claim 14, wherein the mixing mechanism further comprises multiple layers of mesh.

17. The nozzle of claim 14, wherein the venturi comprises a venturi nozzle and a separate venturi diffuser, and wherein the venturi nozzle comprises multiple grooves that act as the ozone inlet ports.

18. The nozzle of claim 14, wherein the nozzle is adapted to produce ozonated water in a single pass directly through the nozzle, wherein the ozonated water comprises an ozone concentration between about 1.5 ppm and about 5 ppm.

19. The nozzle of claim 14, further comprising a seal between the helical mixer and the laminator.

20. The nozzle of claim 14, further comprising an injector cap which holds the laminator and the helical mixer within the nozzle.

* * * * *